US011950919B2

(12) United States Patent
Vialatte et al.

(10) Patent No.: US 11,950,919 B2
(45) Date of Patent: Apr. 9, 2024

(54) SYSTEM FOR REAL-TIME MEASUREMENT OF THE ACTIVITY OF A COGNITIVE FUNCTION AND METHOD FOR CALIBRATING SUCH A SYSTEM (71) Applicants: Paris Sciences Et Lettres—Quartier Latin, Paris (FR); Centre National de la Recherche Scientifique (CNRS), Paris (FR); Ecole Superieure De Physique Et De Chimie Industrielles De La Ville De Paris, Paris (FR); Sorbonne Universite, Paris (FR)

(72) Inventors: François Vialatte, Draveil (FR); Aldo Mora-Sanchez, Kremlin Bicetre (FR); Gérard Dreyfus, Gif s/Yvette (FR); Antoine Gaume, Sceaux (FR); Alfredo Aram Pulini, Paris (FR)

(73) Assignees: Centre National de la Recherche Scientifique (CNRS) (FR); Ecole Superieure e Physique Et De Chimie Industrielles De La Ville De Paris (FR); Sorbonne Universite (FR); Paris Sciences et Lettres (FR)

( * ) Notice: Subject to any disclaimer, the term of this patent is extended or adjusted under 35 U.S.C. 154(b) by 769 days.

(21) Appl. No.: 16/766,087

(22) PCT Filed: Nov. 21, 2018

(86) PCT No.: PCT/EP2018/082109
§ 371 (c)(1),
(2) Date: May 21, 2020

(87) PCT Pub. No.: WO2019/101807
PCT Pub. Date: May 31, 2019

(65) Prior Publication Data
US 2021/0290142 A1 Sep. 23, 2021

(30) Foreign Application Priority Data

Nov. 21, 2017 (FR) .................................... 1760970

(51) Int. Cl.
A61B 5/374 (2021.01)
A61B 5/00 (2006.01)
A61B 5/377 (2021.01)

(52) U.S. Cl.
CPC .............. *A61B 5/374* (2021.01); *A61B 5/377* (2021.01); *A61B 5/7246* (2013.01); *A61B 5/7267* (2013.01)

(58) Field of Classification Search
CPC ...... A61B 5/374; A61B 5/7246; A61B 5/7267
(Continued)

(56) References Cited

PUBLICATIONS

Sanchez et al "A cognitive brain-computer interface prototype for the continuous monitoring of visual working memory load", 2015 IEEE 25th International Workshop on Machine Learning for Signal Processing (MLSP), IEEE, Sep. 17, 2015 (Sep. 17, 2015), pp. 1-5 (Year: 2015).*

(Continued)

*Primary Examiner* — Erin M Piateski
(74) *Attorney, Agent, or Firm* — Lerner David LLP (57) ABSTRACT

The invention concerns a method for calibrating a system for real-time measurement of the activity of a cognitive function of a test subject, the method comprising the successive steps of: acquiring electrical signals representative of a neural activity of a test subject; calculating values of markers of the cognitive function activity; generating a plurality of copies of calculated values of markers and adding noise to the generated copies; and, constructing a classifier by machine learning, based on the calculated marker values and noisy copies, the classifier being suitable for measuring the activity of the cognitive function of the test subject by calculating a probability that an electrical signal representative of the (Continued)

neural activity of the test subject results from a predetermined activity state of the cognitive function of the test subject.

16 Claims, 4 Drawing Sheets

(58) Field of Classification Search
USPC .......................................................... 600/544
See application file for complete search history.

(56) References Cited

PUBLICATIONS

Cecotti et al "Optimization of Single-Trial Detection of Event-Related Potentials Through Artificial Trials", IEEE Transactions on Biomedical Engineering, IEEE Service Center, Piscataway, NJ, USA, vol. 62, No. 9, Sep. 1, 2015 (Sep. 1, 2015), pp. 2170-2176 (Year: 2015).*

Baddeley et al., Working Memory, Psychology of learning and motivation, 1974, pp. 47-89, vol. 8.

Cecotti et al., Optimization of Single-Trial Detection of Event-Related Potentials Through Artificial Trials, IEEE Transactions on Biomedical Engineering, Sep. 2015, pp. 2170-2176, vol. 62, No. 9, XP011666602.

D'Esposito et al., Functional MRI studies of spatial and nonspatial working memory, Cognitive Brain Research, 1998, pp. 1-13, vol. 7.

International Search Report for Application No. PCT/ EP2018/ 082109, dated Feb. 11, 2019, pp. 1-2.

Sánchez et al., A Cognitive Brain-Computer Interface Prototype For The Continuous Monitoring of Visual Working Memory Load, Sep. 2015, IEEE International Workshop on Machine Learning for Signal Processing, Sep. 17-20, 2015, Boston, USA, 5 pages, XP032808434.

\* cited by examiner

SYSTEM FOR REAL-TIME MEASUREMENT OF THE ACTIVITY OF A COGNITIVE FUNCTION AND METHOD FOR CALIBRATING SUCH A SYSTEM

CROSS-REFERENCE TO RELATED APPLICATIONS

The present application is a national phase entry under 35 U.S.C § 371 of International Application No. PCT/EP2018/082109 filed Nov. 21, 2018, which claims priority from French Patent Application No. 1760970, filed Nov. 21, 2017, all of which are hereby incorporated herein by reference.

FIELD OF THE INVENTION

The invention concerns a brain-computer interface, and more particularly a system for real-time measurement of the activity of a cognitive function, and a calibration method for such a system.

STATE OF THE ART

Brain-computer interface (BCI) systems enable communication between the brain and its environment. These systems are used in known ways to allow an individual to interact with their environment by reading and interpreting a subject's brainwaves. Brain-computer interfaces have been more recently used to read or measure cognitive function characteristics.

Mora Sánchez et al. (Mora Sanchez, A. M., Gaume, A., Dreyfus, G., & Vialatte, F. B., 2015, September, *A cognitive brain-computer interface prototype for the continuous monitoring of visual working memory load*, 2015 IEEE 25th International Workshop on Machine Learning for Signal Processing (MLSP), p. 1-5, IEEE) describe a system for assessing the activity of working memory from electrophysiological signals recorded in a database. Calibrating such a system includes the following steps:
- electroencephalogram (EEG) electrophysiological signal acquisition;
- removal of electrophysiological information introduced by reader bias, such as, for example, blinking, manually or automatically by analysis of independent components;
- extraction of marker values dependent on a high or low activity state of working memory, such as, for example, the power measured in a given frequency range, on a given acquisition channel, from electrophysiological signals;
- classification by order of decreasing relevance of markers corresponding to a low or high activity state of working memory and selecting markers among the classified markers;
- construction of a classifier from the marker values selected.

The system is tested and working memory activity is assessed from prerecorded electrophysiological signals, processed by the classifier. These signals are acquired beforehand during a known task executed by a subject, generating low and/or high working memory activity states: it is then possible to test the sensitivity or specificity of the classifier thus constructed.

However, the system described does not allow measuring a subject's cognitive activity in real time, particularly working memory.

Moreover, the signal measured at the classifier output does not allow precise assessment of working memory activity. In particular, the signal measured at the classifier output may depend on the activity of the subject's other cognitive functions during task execution, such as attention or excitation, for example.

Finally, the working memory activity thus assessed may vary and/or present contradictory values depending on the electrophysiological signals tested.

SUMMARY OF THE INVENTION

One objective of the invention is to offer a solution to increase the precision of measuring the activity of a test subject's cognitive function. Another objective of the invention is to measure the activity of a cognitive function, such as working memory, in real time.

These objectives are achieved in the context of the present invention by means of a method for calibrating a system for measuring a test subject's cognitive function activity in real time, the method comprising the following successive steps:
- a) acquiring electrical signals representing a test subject's neural activity during the execution of a first task by the test subject, the first task being configured so that its execution by the subject leads to different activity states of the subject's cognitive function;
- b) calculating marker values for cognitive function from: signals acquired in step a);
  reference electrical signals, each reference electrical signal being representative of the neural activity of a reference subject of a first reference population during the execution of the first task by the reference subject; the marker values being representative of an activity state of the test subject's cognitive function;
- c) generating a plurality of copies of the marker values calculated in step b) and adding noise to the copies generated;
- d) constructing a classifier by automatic learning from the marker values calculated in step b) and the noisy copies calculated in step c), the classifier being suited to measuring the test subject's cognitive function activity by calculating a value representing a probability that an electrical signal representing the test subject's neural activity results from a predetermined activity state of the test subject's cognitive function.

Since noisy copies of the marker values calculated in step b) are generated during step c), it is possible to control the proportion of signals representative of the test subject's neural activity in all the signals so as to reduce the measurement error related to the classifier.

Moreover, since the copies generated in step c) are noisy, the signal variation distribution can be configured to improve classifier statistical learning.

The invention is advantageously supplemented by the following characteristics, taken individually or in any one of the technically-possible combinations thereof:
- the cognitive function is working memory;
- the marker values are representative of a low activity state or a high activity state of the cognitive function of a reference subject;
- after the implementation of step c) and before the implementation of step d), the markers are ordered according to their correlation with the cognitive function activity states, determined from marker values and noisy copies of marker values, then certain markers are selected among the ordered markers according to their rank, step d) being implemented from the values of the selected markers;

step d) is implemented only from the marker values selected or only from the marker values selected and noisy copies of the marker values selected;

the first task is configured so that its execution by a subject leads alternately to at least two different activity states of the subject's cognitive function;

the first task is configured so that its execution by a subject leads alternately to a low activity state and a high activity state of the subject's cognitive function;

a second task is configured so that its execution by the subject leads to simultaneous states of low cognitive function activity and high confusion function activity, the method comprising the steps of:

e) calculating by the classifier of a representative value for a probability that an electrical signal representative of the neural activity of a subject of a second reference population executing the second task, results from the predetermined activity state of the test subject's cognitive function, the electrical signal representative of the neural activity of the subject of the second reference population being then acquired during the execution of the second task by the subject of the second reference population; and f) comparing the value representative of the probability calculated in step e) and a fixed threshold value;

the second task is configured so that its execution by a subject leads alternately to at least two different activity states of the subject's cognitive function;

the second task is configured so that its execution by a subject leads alternately to a low activity and a high activity state of the subject's cognitive function;

the value of one of the markers is a value representative of a spectral power of an electrical signal, calculated over at least part of the signal frequency spectrum;

the part of the signal frequency spectrum is chosen in the $\alpha$ range, the $\beta$ range, the $\gamma$ range and the $\theta$ range;

electrical signals representative of the test subject's neural activity are acquired by means of electrodes arranged in positions Fp1 and/or Cz and/or Oz and/or CP5 of the 10-20 system of the international standard for electrode placement.

Another object of the invention is a method for measuring in real time the activity of a test subject's cognitive function comprising a step of acquiring electrical signals representative of the test subject's neural activity and a step of measuring in real time the activity of the test subject's cognitive function by calculating a value representative of the probability that an electrical signal representative of the test subject's neural activity results from a predetermined cognitive function activity state, using a system for real-time measurement of the test subject's cognitive function activity, the system having been previously calibrated according to a calibration method as defined previously.

Another object of the invention is a system for real time measurement of the activity of a test subject's cognitive function:

a subsystem for electrical signal acquisition;

a processing unit;

characterized in that the processing unit is configured for:

a) acquiring electrical signals representing a test subject's neural activity during the execution of a first task by the test subject, the first task being configured so that its execution by the subject leads to different activity states of the subject's cognitive function;

b) calculating the values of cognitive function activity markers from signals acquired in step a) and reference electrical signals, each reference electrical signal being representative of the neural activity of a reference subject of a first reference population during the execution of the first task by the reference subject and marker values representative of an activity state of the test subject's cognitive function;

c) generating a plurality of copies of the marker values calculated in step b) and adding noise to the copies generated;

d) constructing a classifier by automatic learning from the marker values calculated in step b) and noisy copies calculating in step c), the classifier being suited to measure the cognitive function of the test subject by calculating a value representative of a probability that an electrical signal representative of the test subject's neural activity results from a predetermined activity state of the test subject's cognitive function.

Advantageously, the cognitive function measured by the system is working memory.

PRESENTATION OF THE DRAWINGS

Other characteristics and advantages will appear from the following description, which is purely illustrative and non-limiting and should be read with regard to the attached figures, in which.

DEFINITION

"Working memory" means a cognitive function responsible for temporary information available for processing information. It is described by Baddeley et al. (Baddeley, A. D., & Hitch, G., 1974, *Working memory*, Psychology of learning and motivation, 8, 47-89) as a cognitive model, whose activity can be confirmed, for example, by measurements with magnetic resonance imaging (d'Esposito, M., Aguirre, G. K., Zarahn, E., Ballard, D., Shin, R. K., Et Lease, J., 1998, *Functional MRI studies of spatial and*

*nonspatial working memory*, Cognitive Brain Research, 7(1), 1-13). Working memory depends on the short-term ability to retain information, a few seconds or minutes, to do cognitive operations regarding this information. A subject may have different levels or states of activity (or loads) of working memory depending on the nature of the tasks they execute.

DETAILED DESCRIPTION OF ONE EMBODIMENT

Execution of Tasks by a Subject

Figure 1:
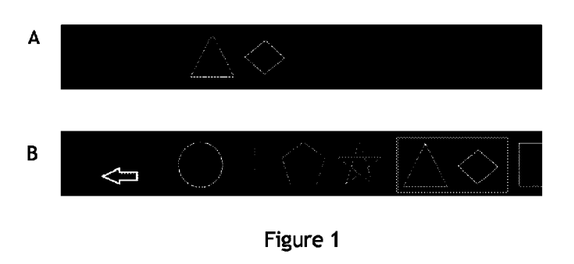
FIG. 1 illustrates the execution of a task specific to working memory.

FIG. 1 illustrates the execution of a first task, specific to a particular cognitive function, in this case working memory. A task specific to working memory is executed, on the one hand, by subjects of a first reference population, and on the other hand by the test subject, during the calibration of system 1 and/or during a measurement of cognitive function activity. The different subjects are placed in front of a computer screen, on which a collection of figures is displayed, the figures being used during the task to be executed. The subjects are asked to allocate a short name to each of the figures so as to familiarize themselves with all the figures. Different sets of figures are shown, and each of the sets corresponds to different semantic fields, such as, for examples, animals or geometrical shapes.

Two conditions or states are tested during the execution of a task: in a low activity state of working memory, a target consists of two figures displayed and in a high activity state of working memory, a target consists of five or six figures displayed.

A target corresponding to one of the states (or to one of the conditions) is shown to the subject. The subject is asked to memorize the target. The target then disappears, and a sequence of figures from the same set slides from right to left on the screen. The scroll speed is 222 pixels per second. The subject is asked to press a button when they find the target in the sequence of figures, which is considered as one test. If the subject presses the button before the target is displayed, or if they miss the target, the test ends and is not analyzed. A test lasts 25 seconds on average. FIG. 1 illustrates a test example in a low activity state of working memory. Panel A of FIG. 1 illustrates a target consisting of two figures: a triangle and a diamond. Panel B of FIG. 1 illustrates the scrolling of a sequence of figures during a test.

A target corresponding to the other state of working memory is then presented to the subject and a test is conducted. The two conditions are alternated. Verbalizing the figures permits a simple storage/recovery method to be used: an internal repetition of the name of the target components, using a phonological loop, allows the subject to compare the target to the scrolling elements. The various subjects are asked to do this internal repetition so that the encoding of information is homogenous among the subjects. Each subject conducts 10 tests from four different semantic fields.

The first task is designed to vary the activity of working memory subfunctions, such as storage, maintenance and/or processing of components. During scrolling, the sequence of figures includes distractors, i.e., sets of figures whose composition is similar to a target. For example, a distractor can be formed by the sequence of target figures in which one figure is changed, from the third figure in order of appearance on the screen. The distractors prevent a subject from memorizing only a part of the target in order to recognize it. The scrolling of the figures is programmed so that a distractor appears with the same probability as a target. This programming prevents the subject from learning and waiting for the appearance of a target following a distractor. The duration of each test is randomly programmed between 15 and 30 seconds so as to prevent the subject from learning the duration of a test. The size of the part of the screen in which the figures scroll is 100 pixels by 300 pixels and the size of each figure is 100 pixels by 100 pixels. This restricted size keeps the subjects' eye movements from generating parasitic electrophysiological signals that are unrelated to cognitive activity. The part of the screen used, the size of the figures and the scroll speed are adjusted so that the subject can only see one figure at a time. The distance between the subject and the screen is 60 cm.

Advantageously, the first task is configured so that its execution by a subject alternatively leads to a low activity state and a high activity state of the subject's cognitive function: thus, an electrical signal drift, independent of the cognitive function studied, can be reduced or avoided.

A transverse task, different from the first task, can also be executed by a subject. The transverse task is used to generate a cognitive function activity in the test subject and designed to be more representative of the tasks conducted by subjects in their daily environment. The transverse task is, for example, a series of mental calculations. For example, a series of digits from $d_1$ to $d_n$ is shown to a subject. The transverse task consists, for example, of multiplying $d_1$ by $d_2$, memorizing the result, then using the result by multiplying it by $d_3$, and so on up to $d_n$.

A second task is also designed, configured to lead to a low activity state of cognitive function and a high activity state of a confusion function, generated by confusion factors. For example, the second task can consist of executing the first task designed to lead to a low activity state of cognitive function in a subject, into which a red dot or a spot is added, following a random trajectory for a period of 1 to 2 seconds. This change relative to the first task generates a high activity state of a working memory confusion factor, such as, for example, attention.

Electrophysiological Signal Acquisition

The electrical signals representative of the neural activity of a test subject or a reference population subject can be electrophysiological signals. As a variant, electrical signals representative of a neural activity of a test subject or a reference population subject can be electrical signals from optical neuroimaging, ultrasound imaging or magnetic imaging, such as, for example, functional magnetic resonance imaging (fMRI), by functional brain ultrasound, by positron emission imaging, and/or by near infrared spectroscopy. Electrophysiological signals are recorded on the test subject or on one or more reference populations, by using an EEG device (Brain Products V-Amp, registered trademark) at a sampling frequency of 500 Hz. As a variant, the electrical signals representative of a test subject's neural activity can be electrophysiological signals measured by electrocardiogram (ECG), by electromyogram, (EMG, measurement representative of muscle activity), by electrooculogram (EOG, measurement representative of a difference in electrical potential in the eye), by magnetoencephalogram (MEG) and/or by a blood pressure sensor, and/or by a respiration sensor. The electrical signals representative of a test subject's neural activity may result from a combination of electrical signals representative of a test subject's neural activity described previously.

Figure 2:
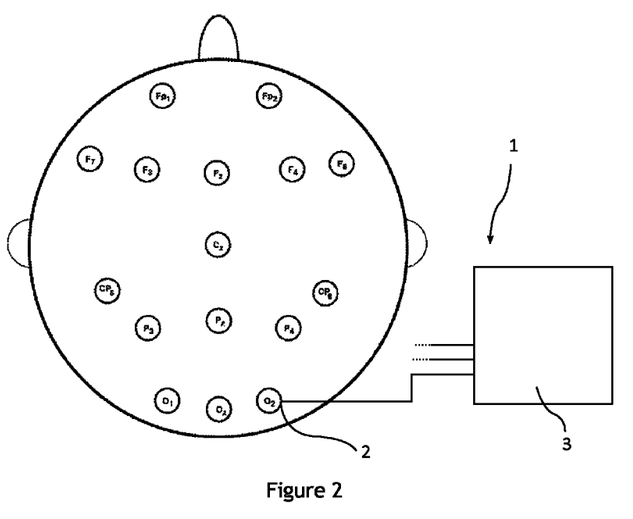
FIG. 2 illustrates a real-time measurement system for a cognitive function activity.

FIG. 2 illustrates a system 1 for real-time measurement of the activity of a test subject's cognitive function comprising a subsystem 2 for acquisition of electrophysiological signals and a processing unit 3. Acquisition subsystem 2 comprises, for example, an EEG headset, EEG electrodes and connectors for connecting the EEG electrodes to processing unit 3. FIG. 2 also illustrates the arrangement of the EEG electrodes around the test subject's skull, according to the 10-20 system international standard.

Electrical signals from a reference population are acquired from 20 healthy subjects, between age 21 and 31, including 10 men and 10 women. Electrical signals for real-time measurement of cognitive function activity are also acquired in this population. Electrical signals are also acquired in 6 subjects executing a transverse task. Following each task, the mental fatigue of each subject is collected and the testing is stopped if the answer is positive.

The EEG signal sequences analyzed last 2.5 seconds. 1744 distinct signals are used as reference electrical signals when calibrating real-time measurement system 1 and 90 distinct signals are used as electrical signals representative of a test subject when calibrating real-time measurement system 1, for each of the subjects. When measuring the activity of a cognitive function in real time, the electrical signals representative of the test subject's neural activity consist of a continuous flow of EEG signals acquired in real time.

Design and Calibration of the Brain-Computer Interface

A set of parameters $P_1, P_2, P_3, P_4$ and $P_5$, for example, can characterize the design of the brain-computer interface. For example, the duration $P_1$ of the reference electrical signal sequences is chosen to be equal to 2.5 seconds. The number $P_2$ of electrical signals representative of the test subject during calibration is chosen to be equal to 90 (45 sequences representative of a high activity state and 45 sequences representative of a low activity state). The proportion $P_3$ of calibration electrical signals from the test subject is equal to 65%. The standard deviation of a Gaussian noise, of zero mean, is equal to $P_4$ multiplied by the standard deviation of the marker considered, where $P_4$ is, for example, equal to 1.5. The number of markers $P_5$ is equal to 8. The standard deviation of a marker considered is, for example, calculated from the values of a marker, itself calculated from electrical signals corresponding to different measurement sequences in time, during the execution of a task.

Figure 3:
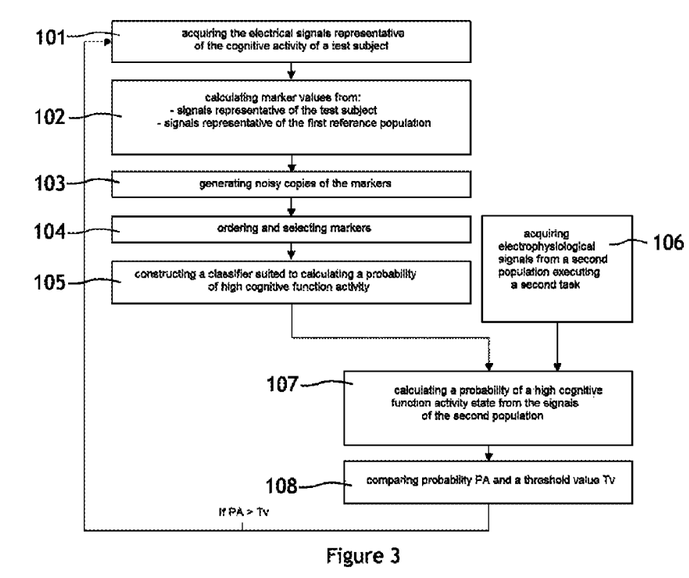
FIG. 3 illustrates a method for calibrating a real-time measurement system of the activity of a test subject's cognitive function according to one embodiment of the invention.

FIG. 3 illustrates a method for calibrating a real-time measurement system of the activity of a cognitive function of a test subject according to one embodiment of the invention. The cognitive function measured by the system is advantageously working memory.

During a method step 101, the acquisition of signals representative of the test subject's cognitive activity is implemented during the execution of the first task by the test subject. The first task is a task specific to the cognitive function measured by system 1: it may, for example, be a task specific to working memory.

Prior to calibration, reference electrical signals were acquired and transmitted to measurement system 1. Each reference electrical signal is representative of the neural activity of a reference subject for a first reference population during the execution of the first task by the reference subject. For example, the task specific to working memory described previously leads to a low activity state or a high activity state of the subject's working memory, depending on the test, when executed by the subject. Acquired signal frequencies below 1 Hz and above 45 Hz are erased from the EEG signals using a third order Butterworth filter. The acquired EEG signals are then segmented into several sequences of a duration equal to $P_1$ seconds. Each sequence is inspected visually and all the sequences comprising too much noise or in which muscle biases are visible are not taken into account. In particular, sequences comprising blinking characteristics are not taken into account.

During a method step 102, the values of the cognitive function activity markers are calculated from signals representative of a test subject's neural activity and reference electrical signals. Each signal is segmented into sequences. The value of a spectral marker is calculated for each sequence using the Welch method, with a 0.5 second window. The values of the spectral markers are calculated in absolute power and in relative power in each of the following frequency ranges: $\delta$ (from 1 to 4 Hz), $\theta$ (from 4 to 8 Hz), $\alpha$ (from 8 to 12 Hz), low $\beta$ (from 12 to 20 Hz) and high $\beta$ (from 20 to 30 Hz). The relative power in a frequency range is the ratio of the power in a frequency range to the power for the set of frequencies. The use of relative power as a marker allows comparing the markers among different test subjects in a more relevant way than the use of absolute power would allow. For each sequence, a total of 192 markers is obtained from 16 acquisition channels, two markers per frequency range and 6 frequency ranges.

It is possible to present the set of marker values calculated in the form of a matrix of 192 lines and M columns, in which M is the number of sequences. This matrix can be combined with a vector whose components are binary, and describe a high activity state or low activity state of the cognitive function tested specifically by the task.

During a method step 103, a plurality of copies of the marker values calculated in method step 102 are generated. Noise is added to the copies generated. Generally, when calibrating a system 1 for real time measurement, at least two types of electrical signals may be used to calculate the marker values, as implemented in method step 102: signal values representative of the neural activity of a test subject and reference electrical signals representative of the neural activity of a reference subject of a first reference population. Subsequently, a classifier is trained with the marker values and noisy copies potentially originating from the two types of signals. Nevertheless, the higher the number of signals originating from a first reference population, the lower the influence of calibration signals originating from the test subject: the precision of classifying the test subject's electrical signals by the classifier may then be insufficient. Thus, by generating noisy copies of marker values, and preferentially marker values of electrical signals representative of a test subject's neural activity, it is possible to control the proportion of marker values issued from signals representative of a first reference population with regard to all the marker values: it is possible, for example, to limit its proportion.

Moreover, the addition of noise to marker values originating from signals representative of a test subject permits simulating a marker variation distribution, compatible with classifier statistical learning. The noise added to each of the copies is, for example, a Gaussian noise of zero mean, and whose standard deviation is equal to $P_4$ times the standard deviation of a marker considered. Thus, it is possible to minimize the error at the output of a classifier by adjusting the proportion of marker values originating from signals representative of the test subject's neural activity with regard to all of the signals used (controlled by parameter $P_3$), and by adjusting the noise added to the different copies (for example controlled by parameter $P_4$).

During a method step 104, the markers used in step 102 are ordered according to their correlation with the activity state(s) of the cognitive function predefined by the first task, determined from marker values and noisy copies of marker values. For example, a Gram-Schmidt orthogonalization (OFR, orthogonal forward regression) can be used, or, generally, supervised methods of selecting variables to order the markers. The first marker, after classification, is the marker whose value(s) have the highest correlation with the cognitive function activity state. The second marker, after classification, is the marker whose value(s) have the highest correlation with the cognitive function activity state after removing from the data the part associated with the first marker, and so on. Then a number of markers are selected among the most relevant according to the order defined previously. It is possible to test the error of a classifier constructed with a given set of markers as described in step 105: a previously-defined number of markers can be selected and the number of components to be selected from the most relevant can be optimized by testing classifier error so as to reduce its error.

During a method step 105, a classifier is built after automatic learning from the calculated marker values and generated noisy copies. Preferentially, the classifier is constructed from at least the marker values selected in step 104 and preferentially only from the marker values selected in step 104 and noisy copies of the marker values selected in method step 104. A classifier may, for example, be a linear discriminant analysis classifier. Classifier learning is also carried out with the activity state of the cognitive function that is associated with each of the selected patterns (low or high activity state, for example).

After learning, the classifier can have an output signal allowing the measurement of the activity of the test subject's cognitive function by calculating a probability PA that an electrical signal representative of the subject's neural activity results from a high activity state of the test subject's cognitive function, or, more generally, a value representative of probability PA, such as a binary result calculated from probability PA. It is also possible to construct a classifier with n classes, n being a natural whole number, able to characterize n states. In this case, the patterns and pattern values corresponding to each of the n cognitive function activity states will have been calculated beforehand, and the first task is configured so that its execution by the subject generates an activity state of subject's cognitive function from a first reference population among the n possible states. The markers are thus used to predict the state(s) of a test subject's cognitive function by an algorithm using the values of these markers.

Figure 4:
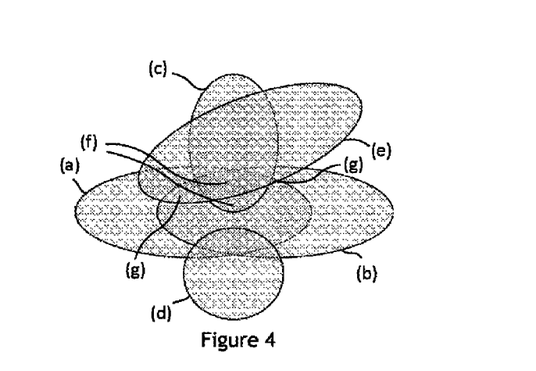
FIG. 4 schematically illustrates the fields of activity of working memory, the cognitive function activity generated by different tasks and the cognitive function activity generated by confusion factors.

FIG. 4 schematically illustrates all the markers, in a finite number, able to measure the activity states of cognitive functions during the execution of a predetermined task. The task specific to the cognitive function measured is designed in such a way as to lead to two distinct cognitive function states in a subject, in this case a low activity state and a high activity state. In practice, the cognitive function measured, such as working memory, can be a complex multimodal construction. The different signals acquired may have been generated by confusion factors. These confusion factors can be cognitive: attention, excitation and/or frustration can be confusion factors with regard to working memory. These confusion factors may also result from motor events, such as blinking, subvocalizations and muscle contractions.

The area defined by ellipse (a) schematically illustrates all the markers representative of the execution of a first task, specific to cognitive function. The area defined by ellipse (b) schematically illustrates all the markers representative of the execution of a transverse task. The area defined by ellipse (c) schematically represents all the markers that allow measuring the activity state of a cognitive function, in this case working memory. The area defined by ellipse (d) schematically represents all the markers that enable measuring the activity state generated by motor confusion factors, and the area defined by ellipse (e) schematically represents all the markers that enable measuring the activity state generated by cognitive confusion factors.

The overlap of ellipses (a) and (b) schematically illustrates a non-empty set of markers representative of the execution of the first task and the transverse task. The overlap of ellipses (a), (b) and (c) (area denoted (f) in the figure) schematically illustrates a non-empty set of markers representative of the execution of the first task, the transverse task and working memory. The fact that this set is not empty results from the fact that the first task and the transverse task were designed to involve working memory. The overlap of ellipses (a), (b) and (e) (area denoted (g) in the figure) schematically illustrates a non-empty set of markers representative of the execution of the first task and the transverse task, and markers that enable measuring the activity state generated by cognitive confusion factors. Preferentially, the markers belonging to this last set are not taken into account when constructing a classifier suited to measuring the activity state of a cognitive function generated by executing the first task or the transverse task.

Thus, it is possible to test the dependence of the cognitive function activity measurement on one or more confusion factors. To this end, during method step 107, the probability PA is calculated with the classifier, for example constructed during method step 105, that an electrical signal representative of the neural activity of a subject of a second reference population, performing the second task, results from a high activity state of the test subject's cognitive function (the electrical signal representative of a neural activity of a subject from a second reference population having been acquired during the execution of the second task by the subject of the second reference population). Electrical signals from a second reference population executing the second task may be acquired beforehand, for example during step 106.

During a method step 108, the probability PA obtained can be compared to a threshold value $T_v$ recorded beforehand, or determined by a user. Thus, if probability PA is greater than 0.5, preferentially greater than 0.6, and preferentially greater than 0.7, then the classifier indicates a high activity state of cognitive function, while the task is specifically designed to cause a low activity state of cognitive function. This test reveals a construction of the classifier that does not permit discriminating a high activity state of cognitive function and the confusing factor. This step may be followed, for example, by a new step of acquiring electrical signals from the subject, so as to arrive at the construction of a new classifier suited to discriminate cognitive function from confusion factors, as illustrated by FIG. 3 for condition $PA > T_v$. This test may also be followed by stopping the measurement.

Real-Time Measurement of Cognitive Function Activity

Figure 5:
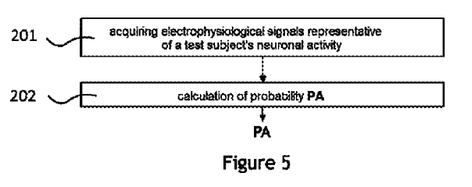
FIG. 5 illustrates a method for real-time measurement of cognitive function activity.

FIG. 5 illustrates a method for real-time measurement of cognitive function activity. A method for measuring cognitive function activity in real time is preceded by a calibration of measurement system 1, for example according to a method comprising steps 101 to 106 of the calibration method: a classifier is constructed so as to be suitable for measuring the test subject's cognitive function activity by calculating a probability PA that an electrical signal representative of the test subject's neural activity results from a high activity state of the test subject's cognitive function.

During step 201 of the real-time measurement method, electrical signals are acquired representative of the test subject's neural activity. A continuous flow of electrical signals is transmitted from acquisition subsystem 2 to processing unit 3 and analyzed by processing unit 3. For example, signals included in a sliding window with a duration of 2.5 seconds are used.

During a method step 202, the probability PA, or more generally, a value representative of probability PA is calculated using real-time measurement system 1 for the test subject's cognitive activity. "Real time" means a measurement of cognitive activity implementing the calculation of probability PA in less than 10 seconds, and preferentially in less than 5 seconds. The value representative of probability PA may, for example, be a binary prediction calculated from probability PA.

Results

Figure 6:
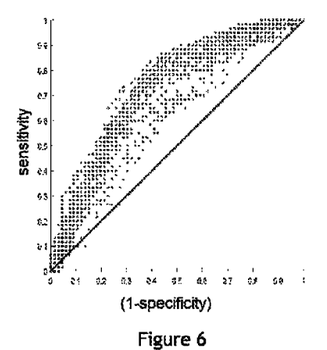
FIG. 6 illustrates the performance characteristic of the classifier corresponding to the execution of the task specific to working memory in real time.

FIG. 6 illustrates the performance characteristic of the classifier, or receiving operating characteristic (ROC) curve corresponding to the execution of the first task, specific to working memory in real time. The value of probability PA is continuously measured for the duration of each test of the first task. Two parameters can be calculated from the ROC curve: the classification threshold and the sustained activity time required. The sustained activity time required is the time during which the cognitive activity function is higher than a threshold value to classify a test as having a high activity state of cognitive function. Thus, for each classification limit and for each sustained activity time required, it is possible to calculate a pair corresponding to specificity and sensitivity, the values of which are illustrated by the points of FIG. 6. For a required specificity value, it is then possible to find a classification limit and an optimal time required for sensitivity to be maximized. The required values of sustained activity time are different according to the test, but on average, an optimal value for this time is comprised between 2 seconds and 10 seconds, preferentially between 4 seconds and 6 seconds, and preferentially substantially equal to 5 seconds. The area under the curve (AUC) in real time is 0.78, higher, with $p<0.0001$, than the value 0.5 corresponding to a random classifier, illustrated by the black line in FIG. 6.

A total of 92 tests were analyzed, in which electrical signals led to concluding a response in agreement with the task executed (good response) in 82% of cases. The individual data are summarized in Table 1 below:

TABLE 1

| subjects | tests with no response | noisy tests removed | total tests analyzed | good responses |
|---|---|---|---|---|
| 1 | 1 | 1 | 18 | 83% |
| 2 | 3 | 0 | 17 | 76% |
| 3 | 0 | 0 | 20 | 85% |
| 4 | 0 | 0 | 10 | 100% |
| 5 | 1 | 0 | 19 | 73% |
| 6 | 7 | 5 | 8 | 75% |
| total | 12 | 6 | 92 | 82% |

Figure 7:
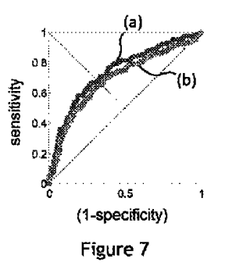
FIG. 7 illustrates the performance characteristics of the classifier during the execution of a task by a subject in the presence of a high activity state of the confusion factor.

FIG. 7 illustrates the performance characteristics of the classifier during the execution of a task by a subject in the presence of a high activity state of the confusion factor (in this case, excitement). Curve (a) is the performance characteristic of a classifier during the execution of a task by a subject in the presence of a high activity state of the confusion factor and curve (b) is the same characteristic corrected, after decorrelating the information included in the excitation markers. The area under curve (b) is less than 7% of the area of curve (a), which does not representative a significant difference.

Figure 8:
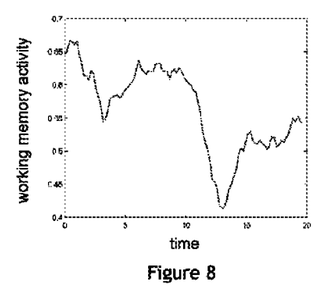
FIG. 8 illustrates the evolution of the probability that an electrical signal representative of the test subject's neural activity results from a high activity state of the test subject's cognitive function in time.

FIG. 8 illustrates the evolution of probability PA over time corresponding to the activity of working memory. The mean of probability PA measured in 20 tests during execution of a transverse task is illustrated as a function of time. Probability PA generally shows a decrease after 10 seconds. This variation is consistent given the switching of the working memory activity state, from high to low, at 8.5 seconds and the delay introduced by system 1 of substantially 2.5 seconds. In other words, the measurement of probability PA is an overall measurement of working memory activity during the 2.5 seconds that precede the time at which probability PA is measured. Generally, after reaching a minimum value, probability PA increases again, without reaching values as high as during the period corresponding to a high activity state of working memory.

Figure 9:
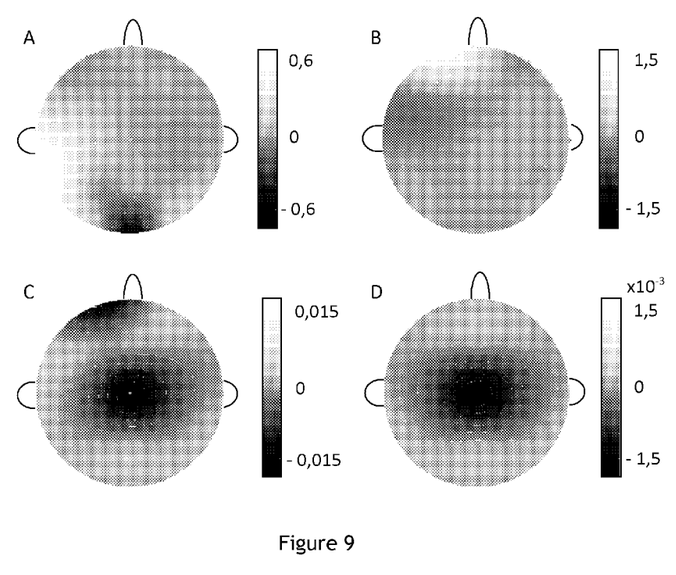
FIG. 9 illustrates the difference between marker values for a low activity state and a high activity state for different channels.

FIG. 9 illustrates the difference of the marker values between a high activity state and a low activity state for different frequency ranges. Panel A of FIG. 9 illustrates the difference between, on the one hand, a mean of the spectral power in the $\alpha$ frequency range, for all the channels, during the execution of a task corresponding to a high activity state of working memory, and, on the other hand, the corresponding mean in a low activity state. Panel B of FIG. 9 illustrates the difference between, on the one hand, a mean of the spectral power in the low $\gamma$ frequency range, for all the channels, during the execution of a task corresponding to a high activity state of working memory, and, on the other hand, the corresponding mean in a low activity state. Panel C of FIG. 9 illustrates the difference between, on the one hand, a mean of the spectral power in the low $\beta$ frequency range, for all the channels, during the execution of a task corresponding to a high activity state of working memory, and, on the other hand, the corresponding mean in a low activity state. Panel D of FIG. 9 illustrates the difference between, on the one hand, a mean of the spectral power in the high $\beta$ frequency range, for all the channels, during the execution of a task corresponding to a high activity state of working memory, and, on the other hand, the corresponding mean in a low activity state. The mean of the measured spectral powers is calculated by integrating the powers for 10 seconds. The frequency ranges illustrated are frequency ranges for markers selected, for example by a method described by method step 105 of the calibration method illustrated in FIG. 3. The markers selected can preferentially be chosen from the relative power of the low $\beta$ range acquired by an electrode arranged at position Fp1, as described by the 10-20 system standard, the relative power of the low $\beta$ range acquired by an electrode arranged at position Cz, the relative power of the low $\gamma$ range acquired by an electrode arranged at position Fp1, the relative power of the high $\beta$ range acquired by an electrode arranged at position Cz, the relative power of the $\alpha$ range acquired by an electrode arranged in position Oz and the relative power of the $\alpha$ range acquired by an electrode arranged in position CP5.

Proposed system 1, as well as the methods for calibrating system 1 and measuring cognitive function in real time, advantageously find their application in:

control and monitoring of working memory activity when driving vehicles (automobile, aviation, navigation, rail transport, and military transport, including submarines);

the training of cognitive functions dependent on working memory, such as school learning;

control and/or training of workload activity for the prevention of medical disorders;

more generally, personal control of working memory activity during any sort of activity (neurofeedback).

The invention claimed is:

1. A method for calibrating a system for real-time measurement of an activity of a cognitive function of a test subject, wherein the cognitive function is a working memory, the method comprising the following successive steps:
   a) acquiring electrical signals representing a neural activity of the test subject during an execution of a first task by the test subject, the first task being configured so that the execution of the first task by the test subject leads to different activity states of the cognitive function of the test subject;
   b) determining signal sequences by segmenting the electrical signals acquired in step a), and determining reference sequences by segmenting reference electrical signals, each reference electrical signal being representative of a neural activity of a reference subject during the execution of the first task by the reference subject, the reference subject being part of a first reference population;
   c) determining, by using Welch method, signal marker values from each signal sequence and determining, by using Welch method, reference marker values from each reference sequence, the signal marker values being representative of an activity state of the cognitive function of the test subject and the reference marker values being representative of an activity state of the cognitive function of the reference subject;
   d) generating copies of the signal marker values and generating copies of the reference marker values and adding noise to the copies of the signal marker values and to the copies of the reference marker values so as to respectively produce noisy copies of the signal marker values and noisy copies of the reference marker values;
   e) constructing a classifier by automatic learning from the signal marker values, the reference marker values, the noisy copies of the signal marker values and the noisy copies of the reference marker values, the classifier being configured to measure the activity of the cognitive function by calculating a value representing a first probability that an electrical signal representative of the neural activity of the test subject results from a predetermined activity state of the cognitive function of the test subject.

2. The method according to claim 1, wherein the cognitive function is working memory.

3. The method according to claim 1, wherein the reference marker values are representative of a low activity state or a high activity state of the cognitive function of the reference subject.

4. The method according to claim 1, including after step d) and before step e), a step of:
   determining a first correlation value for each signal marker value, a second correlation value for each reference marker value, a third correlation value for each noisy copy of the signal marker value and a fourth correlation value for each noisy copy of the reference marker value, wherein the first correlation value, the second correlation value, the third correlation value and the fourth correlation value represent respectively a correlation of the signal marker value with the cognitive function activity state, a correlation of the reference marker value with the cognitive function activity state, a correlation of the noisy copy of the signal marker value with the cognitive function activity state, and a correlation of the noisy copy of the reference marker value with the cognitive function activity state;
   ordering the signal marker values and the reference marker values according to respectively the first correlation value and the second correlation value; and
   selecting at least one of the signal marker values based on a rank of the ordered signal marker values and at least one of the reference marker values based on a rank of the ordered reference marker values, wherein step e) is implemented based on the selected signal marker value and the selected reference marker value.

5. The method according to claim 4, wherein step e) is implemented only based on:
   the at least one selected signal marker value and the at least one selected reference marker value; or
   the at least one selected signal marker value, the at least one selected reference marker value, the noisy copies of the at least one selected signal marker value and the noisy copies of the at least one selected reference marker value.

6. The method according to claim 1, wherein the first task is configured so that execution of the first task leads alternately to at least two different activity states of the cognitive function.

7. The method according to claim 1, wherein the first task is configured so that execution of the first task leads alternately to a low activity state and a high activity state of the cognitive function.

8. The method according to claim 1, wherein a second task is configured so that execution of the second task by the test subject leads to simultaneous states, each simultaneous state simultaneously corresponding to a low activity of the cognitive function and a high activity of a confusion function, the method comprising steps of:
   f) calculating, by the classifier, a representative value for a second probability that an electrical signal representative of a neural activity of a second subject executing the second task results from the predetermined activity state of the test subject's cognitive function, the second subject being part of a second reference population, the electrical signal representative of the neural activity of the second subject being then acquired during the execution of the second task by the second subject; and
   g) comparing the value representative of the second probability and a fixed threshold value.

9. The method according to claim 8, wherein the first task is configured so that execution of the first task leads alternately to at least two different activity states of the cognitive function.

10. The method according to claim 8, wherein the second task is configured so that execution of the second task leads alternately to a low activity state and a high activity state of the cognitive function.

11. The method according to claim 1, wherein one of the signal marker values or of the reference signal marker values is a representative value of a spectral power of an electrical signal, the representative value being calculated over a part of the frequency spectrum of the electric signal.

12. The method according to claim 11, wherein the part of the frequency spectrum of the electric signal is chosen among the $\alpha$ range, the $\beta$ range, the $\gamma$ range and the $\theta$ range.

13. The method according to claim 1, wherein electrical signals acquired in step a) are acquired by means of electrodes arranged in positions Fp1 and/or Cz and/or Oz and/or CP5 of a 10-20 system of the international standard for electrode placement.

14. The method according to claim 1,
further comprising:
- a step of acquiring electrical signals representative of a neural activity of the test subject and
- a step of measuring in real time the activity of the cognitive function of the test subject by calculating a value representative of the first probability using a system for real-time measurement of the activity of the cognitive function of the test subject.

15. A system for real-time measurement of an activity of a cognitive function of a test subject, wherein the cognitive function is a working memory, comprising:
- a subsystem for electrical signal acquisition;
- a processing unit;
wherein the processing unit is configured for:
  a) acquiring electrical signals representing a neural activity of the test subject during an execution of a first task by the test subject, the first task being configured so that the execution of the first task by the test subject leads to different states of activity of the cognitive function of the test subject;
  b) determining signal sequences by segmenting the electrical signal acquired, and determining reference sequences by segmenting reference electrical signals, each reference electrical signal being representative of a neural activity of a reference subject during the execution of the first task by the reference subject, the reference subject being part of a first reference population;
  c) determining, by using Welch method, signal marker values from each signal sequence and determining, by using Welch method, reference marker values from each reference sequence, the signal marker values being representative of an activity state of the cognitive function of the test subject and the reference marker values being representative of an activity state of a cognitive function of a reference subject;
  d) generating copies of the signal marker values and generating copies of the reference marker values and adding noise to the copies of the signal marker values and to the copies of the reference marker values so as to produce noisy copies of the signal marker values and noisy copies of the reference marker values;
  e) constructing a classifier by automatic learning from the signal marker values, the reference marker values, and on the noisy copies of the signal marker values and noisy copies of the reference marker values, the classifier being configured to measure the activity of the cognitive function by calculating a value representing a first probability that an electrical signal representative of the neural activity of the test subject results from a predetermined activity state of the cognitive function of the test subject.

16. The system according to claim 15, wherein the cognitive function is working memory.

* * * * *